US008338609B2

(12) United States Patent
Manabe et al.

(10) Patent No.: US 8,338,609 B2
(45) Date of Patent: Dec. 25, 2012

(54) LIGAND, METAL COMPLEX COMPOUND CONTAINING THE SAME, AND METHOD FOR PRODUCING THE SAME, AND METHOD FOR PRODUCING MOLECULAR DEVICE

(75) Inventors: Toshio Manabe, Kawasaki (JP); Fumio Takei, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 274 days.

(21) Appl. No.: 12/469,811

(22) Filed: May 21, 2009

(65) Prior Publication Data

US 2009/0292123 A1 Nov. 26, 2009

(30) Foreign Application Priority Data

May 23, 2008 (JP) ................................. 2008-135466
Dec. 25, 2008 (JP) ................................. 2008-330882

(51) Int. Cl.
*C07D 401/04* (2006.01)
(52) U.S. Cl. .................................................. 546/273.4
(58) Field of Classification Search ................ 546/273.4
See application file for complete search history.

(56) References Cited

U.S. PATENT DOCUMENTS

| 4,689,331 A * | 8/1987 | Ankner et al. ................. 514/338 |
| 4,831,032 A * | 5/1989 | von der Saal et al. ... 514/252.06 |
| 2005/0054849 A1 | 3/2005 | Manabe et al. |
| 2006/0042026 A1* | 3/2006 | Glenn et al. ...................... 8/405 |

FOREIGN PATENT DOCUMENTS

WO 03/078384 A1 9/2003

OTHER PUBLICATIONS

Kotovskaya et. al. "Algorithmic Search for Compounds With Antiviral Activity in a Series of Nitrogen and Sulfur Containing Heterocycles" Pharmaceutical Chemistry Journal 1989, vol. 23, No. 3, pp. 244-248.*
Saunders, K. H. "Syntheses in the Pyrido- and Piperido-(1': 2'-1 : 2)benziminazole Series" Journal of the Chemical Society 1955, 3275-3287.*
Weiss et. al. "Syntheses and Reactions of Polycationically Substituted Azido- and Diazidobenzenes" Eur. J. Org. Chem. 2007, 5270-5276.*
Postovskii et. al. "Benzimidazole Derivatives With Zwitterion Structures" Chemistry of Heterocyclic Compounds 1975, vol. 11, No. 7, pp. 866-868.*
Izakovich and Khidekel "Coordination Compounds of Transition Metals in the Chemistry of Aromatic Nitro-compounds" Russian Chemical Reviews, 57 (5), 1988, 419-432.*
Wolfgang von der Saal et. al. "Nonsteroidal Cardiotonics. 2. The Inotropic Activity of Linear, Tricyclic 5-6-5 Fused Heterocycles" Journal of Medicinal Chemistry 1989, 32, 1481-1491.*
J. R. Heath et al., "A Defect-Tolerant Computer Architecture: Opportunities for Nanotechnology", Science, 1998, pp. 1716-1721, vol. 280.

* cited by examiner

*Primary Examiner* — David K O'Dell
(74) *Attorney, Agent, or Firm* — Westerman, Hattori, Daniels & Adrian, LLP

(57) ABSTRACT

A ligand contains: a benzimidazole skeleton; and functional groups at the 5-position and the 6-position of the benzimidazole skeleton. The functional group is capable of forming a coordinate bond with a metal, and contains a nitrogen atom.

4 Claims, 10 Drawing Sheets

FIG. 5A
FIG. 5B
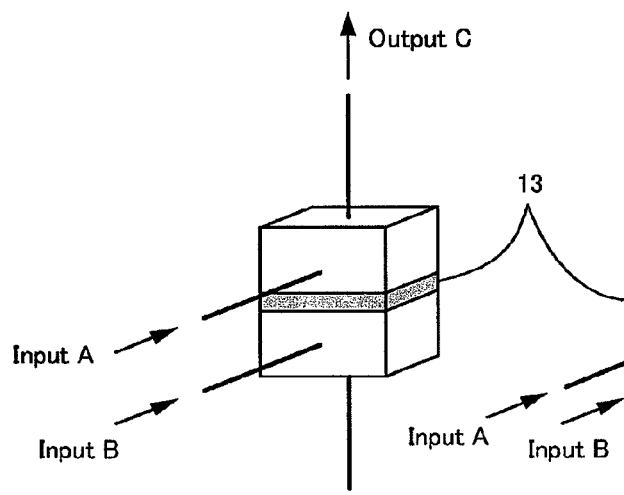
AND Circuit
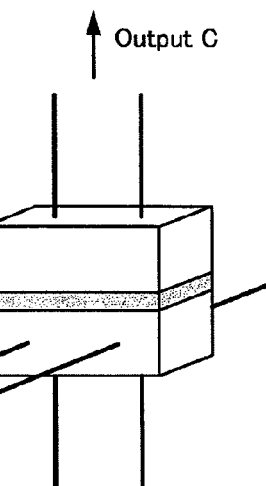
OR Circuit
FIG. 6
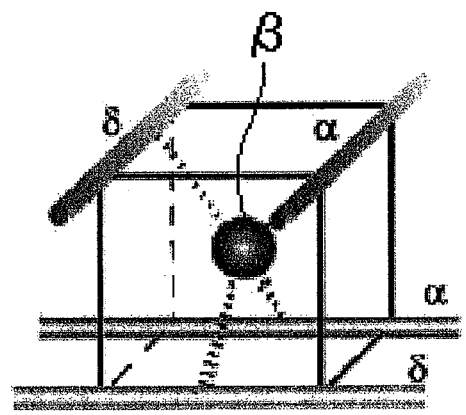

US 8,338,609 B2

LIGAND, METAL COMPLEX COMPOUND CONTAINING THE SAME, AND METHOD FOR PRODUCING THE SAME, AND METHOD FOR PRODUCING MOLECULAR DEVICE

CROSS-REFERENCE TO RELATED APPLICATIONS

This application is based upon and claims the benefits of the priority from the prior Japanese Patent Applications No. 2008-135466 filed on May 23, 2008 and No. 2008-330882 filed on Dec. 25, 2008, the entire contents of which are incorporated herein by reference.

FIELD

The embodiments discussed herein are related to a ligand, a metal complex compound containing the ligand, and a method for producing the metal complex compound, and a method for producing a molecular device.

BACKGROUND

In the field of information and communication, the technologies related to the computer field have relied on an electronic circuit using a semiconductor device. The researches for the semiconductor device have been conducted so as to improve the processing ability by fining a line width of a wire printed on a substrate, or increasing the degree of integration.

However, such fining technology according to the top-down method has a limit due to the quantum theoretical influence. For this reason, attentions have recently been attracted to a molecular element (bottom-up method) in which a molecule or a group of molecules are functioned as a device.

In the design and/or construction of the molecular element and/or an electronic circuit using the molecular element, the problems have been arisen in terms how to realize the positioning/alignment of individual molecules, recognition of each molecule, access to each molecular element, wiring for accurately linking between certain molecular elements and forming a circuit, addressing, and the like. It is not practical to construct the complicated electronic circuit by sifting the positions of individual molecules.

Therefore, the researches and studies have been conducted on the method for constructing a simple structure and providing complicated functions by the control method. For example, so-called "cross bar switch," in which the switching at crossing where nano wires are orthogonally crossed is controlled by the input from the nano wires, is a candidate for a nano device which does not have complicated production process, and researches have been actively conducted thereon (see James R. Heath, Philip J. Kuekes, Gregory S. Snider, R. Stanley Williams, Science vol. 280 (1998)). Expectations for this device are high, as high density devices are easily provided, if arrays formed of the nano wires are constructed at molecular level and in the bottom-up method.

The present inventors et al. have researched for a construction of a wire array structure in which a one-dimensional metal complex chain and a one-dimensional conductive wire formed of a donor or acceptor molecule are aligned, aiming at synthesizing a metal complex integrated structure realizing both a element function and wiring function at the same time by utilizing a self-alignment and/or self-integration of metal complex. Therefore, we have developed various dinuclear metal complexes for use as a building block for the construction of the wire array structure (see International Publication No. WO 03/078384). This dinuclear metal complex realizes switching by crossing molecular chains in the self-forming crystal and/or thin film, and changing electric conductivity of the metal complex chains by the electron transfer at the crossings.

However, in this case, a coupling molecule (conductive wire portion) needs to be introduced separate from the metal complex unit, and the conductive wire is connected with a hydrogen bonding so as to form a metal complex integrated structure using the dinuclear metal complex as a building block. As the metal complex integrated structure is formed from multiple components, the control for alignment may be difficult, or a large conductivity may not be expected.

Moreover, a ligand for forming the dinuclear metal complex is formed of one molecule, and thus the molecular weight thereof naturally becomes large. Therefore, the solubility of the dinuclear metal complex in which a metal is incorporated to the ligand is lowered, and it may be difficult to form a metal complex integrated structure.

SUMMARY

According to an aspect of the invention, a ligand contains a benzimidazole skeleton, and functional groups at the 5- and 6-positions of the benzimidazole skeleton, in which the functional group is capable of forming a coordinate bond with a metal, and contains a nitrogen atom.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

FIG. 5A is a conceptual diagram illustrating an example of a logic circuit (AND circuit) using the metal complex integrated structure, and FIG. 5B is a conceptual diagram illustrating an example of a logic circuit (OR circuit) using the metal complex integrated structure.

FIG. 6 is a schematic diagram for explaining the embodiment of a cross-bar switch.

DESCRIPTION OF EMBODIMENTS (Ligand)

Figure 1:
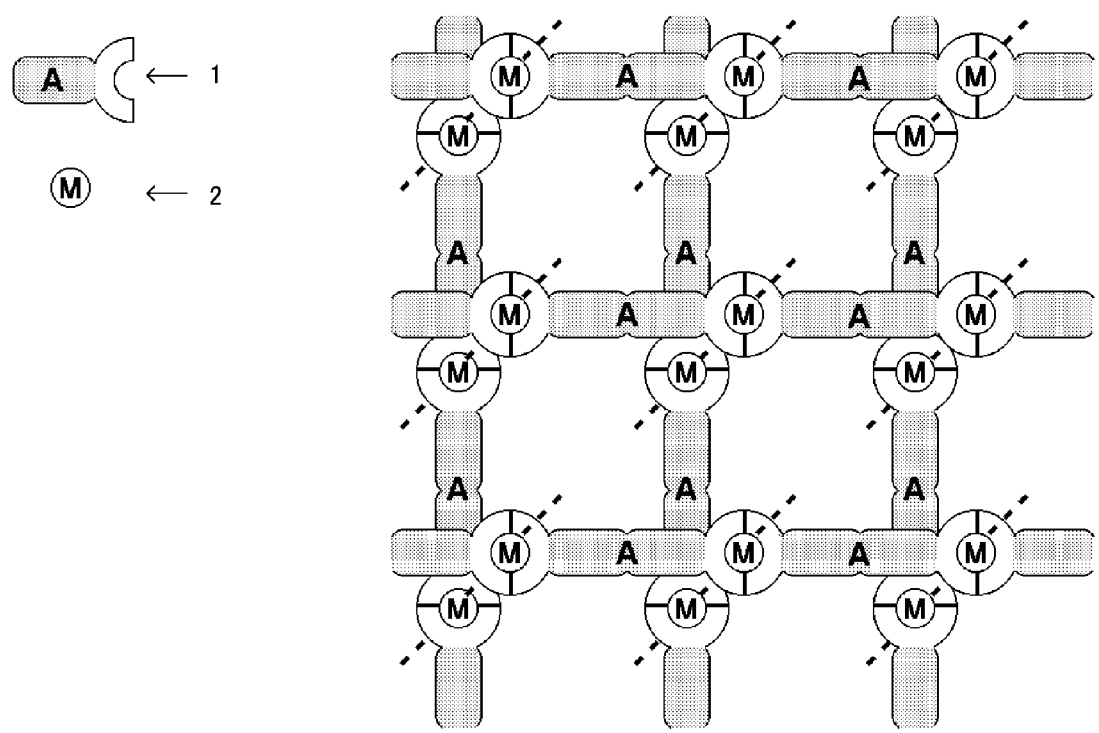
FIG. 1 is a schematic two-dimensional view illustrating an example of a metal complex integrated structure.

The ligand contains a benzimidazole skeleton and a conductive wire portion, and may further contain a substituent and the like, as necessary.

<Benzimidazole Skeleton>

The benzimidazole skeleton is suitably selected depending on the intended purpose without any restriction. Examples thereof include a benzimidazole skeleton to which a pyridinium derivative, e.g. a pyridinium group, a bromopyridinium group, and 4-4'bipyridinium group, is introduced. In view of the conductivity, a benzimidazole skeleton to which a 4-4'bipyridinium group is introduced is preferable.

The Br terminals of the benzimidazole skeleton to which the bromopyridinium group is introduced are bound to other benzimidazole skeletons by electrolytic polymerization.

The nitrogen atom present in the 4-4'bipyridinium group has a function to connect the metal complex compound, which will be described later, with another metal complex compound by directly coordinating with a metal.

<Functional Group>

The functional groups are suitably selected depending on the intended purpose without any restriction, provided that they are introduced at the 5-position and the 6-position of the benzimidazole skeleton, are capable of forming a coordinate bond with a metal, and each contain a nitrogen atom. For example, the functional group is preferably an amino group. The functional groups may be identical to each other or may be different to each other, but it is preferable that two amino groups are present as the functional groups.

<Substituent>

The substituent is suitably selected depending on the purpose without any restriction. For example, the substituent is preferably at least one selected from the group consisting of an alkyl group, alkoxy group, aryloxy group, hydroxyl group, thiol group, amino group and halogen atom.

Examples of the alkyl group include a methyl group, ethyl group, propyl group and butyl group.

Examples of the alkoxy group include a methoxy group, ethoxy group, propoxy group and butoxy group.

Examples of the halogen atom include fluorine, chlorine, bromine and iodine.

Specific examples of the ligand include the compounds expressed by the following formulae (1) to (3).

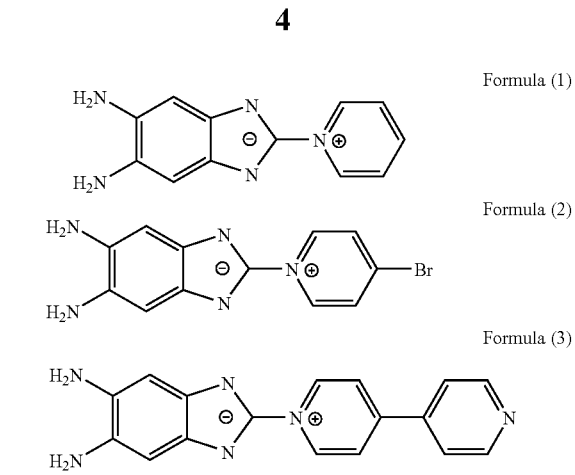

The ligand forms a metal complex (e.g., the metal complex represented by the following formulae (4) and (5)) with a central metal ion, and a metal complex integrated structure is formed by building up the metal complex as a building block. The ligand is suitably used for constructing a nano-scale device of ultra-high density and ultra-high speed, such as a molecular element, a matrix circuit, a molecular functional device, a logic circuit and the like, suitable used in computing units, displays, memories, etc. in the information and communication field, and suitable for making each of the aforementioned elements, devices and units minute and precise.

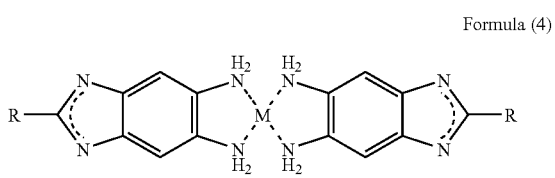

Note that, R is

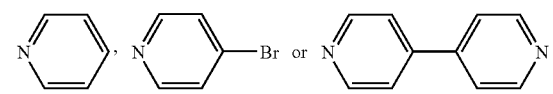

and, M is $Ni^{2+}$, $Pd^{2+}$, or $Zn^{2+}$.

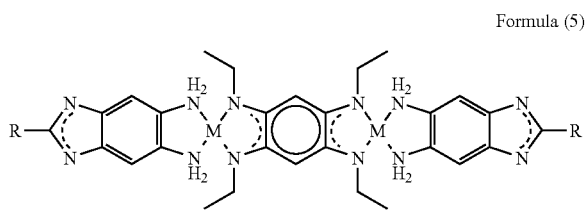

Note that, R is

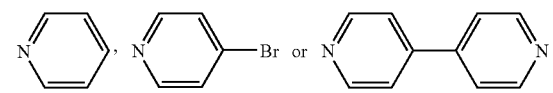

and M is $Ni^{2+}$, $Pd^{2+}$, $Pt^{2+}$, or $Zn^{2+}$.

The ligand can be synthesized in accordance with an arbitrarily selected method.

In the ligand, the benzimidazole skeleton has been previously introduced at the terminal of the ligand. The introduced benzimidazole skeleton interacts with that in other ligands at the time when the ligands are integrated, and functions as a conductive wire portion. Accordingly, there is no need to introduce coupling molecules thereto, and a metal complex integrated structure is constructed using only a metal complex unit as a building block.

In the ligand, moreover, a plurality of the ligands is coordinated with one metal, thus making the molecular weight of the ligand small.

(Metal Complex Compound and Production Method Thereof)

The metal complex compound is represented by the following formula (4).

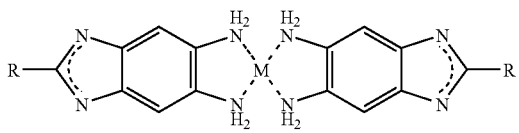

Formula (4)

Note that, R is

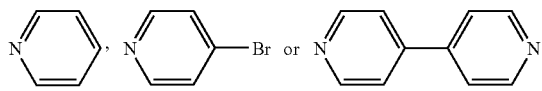

and, M is $Ni^{2+}$, $Pd^{2+}$, or $Zn^{2+}$.

The method for producing the metal complex compound contains at least a mixing step and a condensing step, and optionally contains arbitrarily selected other steps as needed.

—Mixing Step—

The mixing step is to mix the ligand and a metal-contained solution so as to prepare a mixed solution.

The metal contained in the metal-contained solution is suitably selected depending on the intended purpose without any restriction. Examples of such metal include Ni, Pd, Pt, Zn, and the like.

—Condensing Step—

The condensing step is to condense the mixed solution. By condensing the mixed solution, a metal complex compound is yielded.

A metal complex of nickel or the like is synthesized by using the novel ligand (Formulae (1) to (3)) in which a pyridinium derivative is introduced at the 2-position of 5,6-diaminobenzimidazole skeleton based on the aforementioned molecular design. In this manner, a material suitable for the formation of a molecular wire can be attained. The metal complex compound (Formula (4)), which has imidazole and pyridinium in the ligand, has desirable characteristics for inducing electron transfer, and is expected to exhibit a switching function when used for a molecular element.

In the metal complex compound, the benzimidazole skeleton has been introduced at the terminal of the ligand, and the introduced benzimidazole skeleton interacts with that in other ligands at the time when the metal complex compound is integrated, and functions as a conductive wire portion. Accordingly, there is no need to introduce coupling molecules functioning as a conductive wire portion thereto, and a metal complex integrated structure is constructed using only a metal complex unit as a building block.

In the metal complex compound, moreover, a plurality of the ligands are coordinated with one metal, thus making the molecular weight of the ligand, as a starting material, small, which render the molecular weight of the metal complex compound small.

In the method for producing the metal complex compound, the ligand and the metal-contained solution are mixed to prepare a mixed solution in the mixing step, and the mixed solution is condensed in the condensing step. As a result, the metal complex compound can be efficiently attained.

(Method for Producing Molecular Device)

The method for producing a molecular device contains at least a self-aligning and/or self-integrating step, and optionally contains arbitrarily selected other steps as needed.

—Self-Aligning and/or Self-Integrating Step—

The self-aligning and/or self-integrating step is to self-align and/or self-integrate the metal complex compound. As a result of the self-alignment and/or self-integration of the metal complex compound, a metal complex integrated structure in which interactions between the molecules and alignments of the molecular chains are controlled at a certain intended order.

The method for producing the metal complex integrated structure is suitably selected depending on the intended purpose without any restriction. For example, it is produced in such manner that the solution containing the metal complex compound is crystallized and/or formed into a film by an electrolytic reaction (electrosynthesis) and/or Langmuir Blodgett (LB) method.

In accordance with the method using the electrolytic reaction (electrosynthesis), the metal complex compound and other components are dissolved in a solvent, e.g. alcohol, and the obtained solution is subjected to electrolysis to thereby deposit a metal complex integrated structure in which metal complex chains are integrated on the electrode.

The electrode for use in the electrolytic reaction (electrosynthesis) is, for example, a platinum wire, a platinum plate, a glass plate on which ITO is deposited, or the like. Moreover, tetrabutylammonium or the like is used as a supporting electrolyte.

In the course of the crystallization and/or formation of a film, the metal complex compound is self-integrated. In the method of the present embodiment, the crystallization and/or formation of a film may be carried out repeatedly.

Moreover, the metal complex integrated structure may be formed by using the characteristics such that the metal complex is regularly self-aligned and self-integrated in a solid due to the various interactions (chemical bonding and/or, self-aligning and/or self-integrating of molecules).

In this case, the metal complex compound is aligned by the interactions (various bonds and the like) in such manner that the aligned compounds become electrically conductive, and two-dimensional or three-dimensional network structure is formed at once. Therefore, the metal complex integrated structure having a monocrystal and/or thin film structure is efficiently produced.

In the method for producing the molecular device, the metal complex compound is self-aligned and/or self-integrated in the self-aligning and/or self-integrating step. As a result, a molecular device of high density can be easily obtained.

The embodiment of the metal complex integrated structure, such as a monocrystal and/or thin film, can be arbitrarily designed by arbitrarily controlling the production conditions, combination of materials for use, and the like. By integrating the metal complex integrated structure as a basic unit, a molecular element which has a fine, precise, uniformed and accurate structure is efficiently formed in the manner of bottom-up formation order.

—Application of Metal Complex Integrated Structure to Molecular Device—

The metal complex integrated structure is suitably applicable to a molecular device such as a molecular element of nano-scale, a matrix circuit, molecular functional device, a logic circuit and the like, as described below.

<Molecular Element>

Since the metal complex integrated structure has the aforementioned structure and functions, it is applicable to a molecular element. In the case where the metal complex integrated structure is applied to the molecular element, the molecular element has a monocrystal and/or thin film structure in which metal complex chains, each of which is formed of metal ions and ligands functioning as a conductive wire portion, are crossed each other, and the ligands (conductive wires) in the metal complex chains are extended to the edge of the monocrystal and/or thin film. Therefore, electrons are transferred from the ligands (conductive wires) to the metal complex chains, as a voltage is applied to the ligands (conductive wires) and an electric signal is transmitted. As a result, a density of carrier to be injected to the metal complex chains is controlled externally relative to the monocrystal and/or thin film, and the electrical conductivity of the metal complex chains in the direction of the integration can be suitably controlled. Accordingly, it is possible to design a fine molecular element of molecular-scale, having a switching element function, without any problems of wiring.

<Matrix Circuit>

Figure 2:
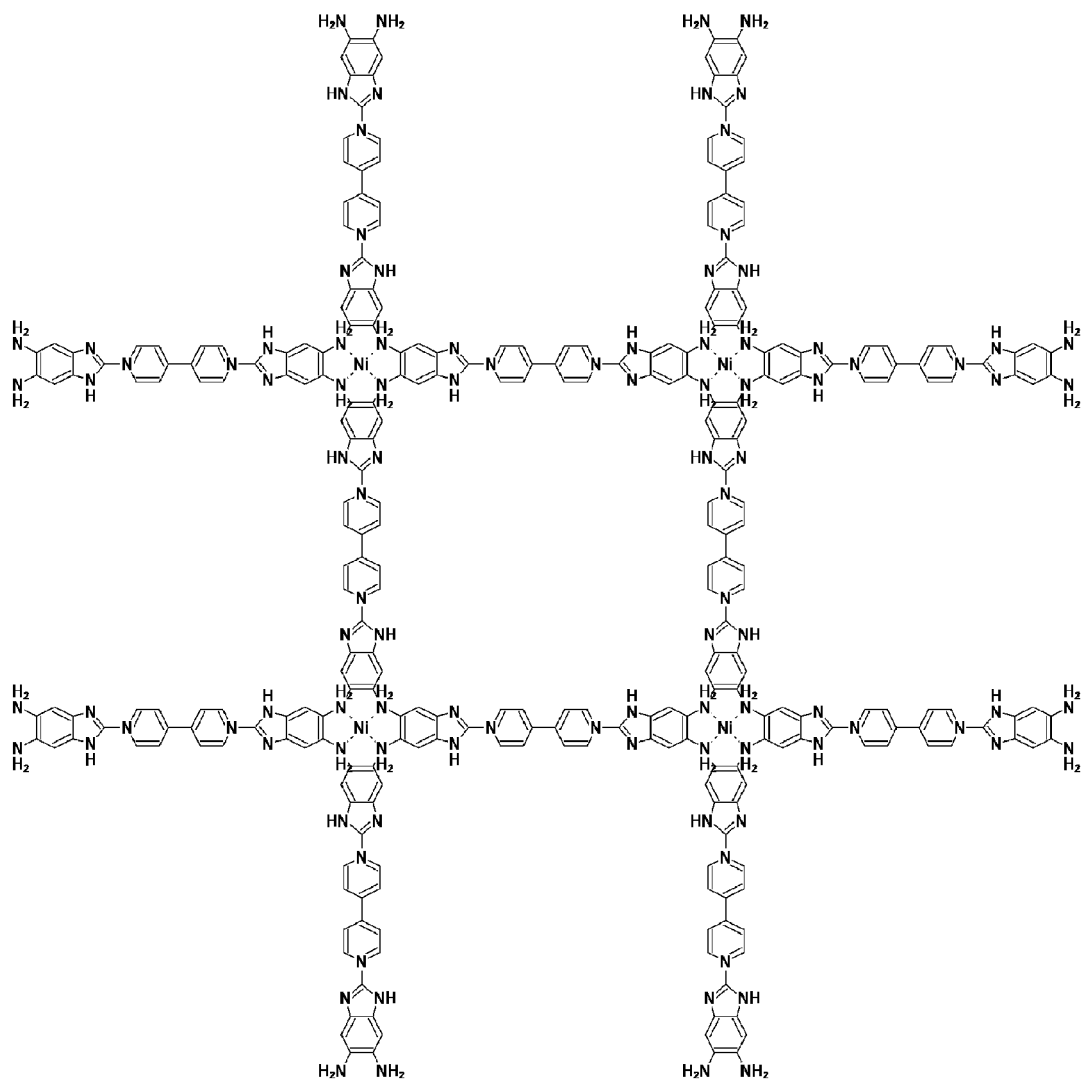
FIG. 2 is a schematic view illustrating an example of a matrix circuit (the metal complex integrated structure) using a metal complex chain.

Since the metal complex integrated structure has the aforementioned structure and functions, it is applicable to a matrix circuit. In the case where the metal complex integrated structure is applied to the matrix circuit, for example, a matrix circuit having a three-dimensional network structure as illustrated in FIG. 1 and FIG. 2 is formed by orthogonally crossing metal complex chains in which the ligands 1 are connected with the metal ions 2 (e.g. Ni ions). The three-dimensional network structure of the matrix circuit is a monocrystal and/or thin film formed by the self-alignment and/or self-integration of the metal chains, and the metal complex chains are extended to the edges of the monocrystal and/or thin film.

Figure 3:
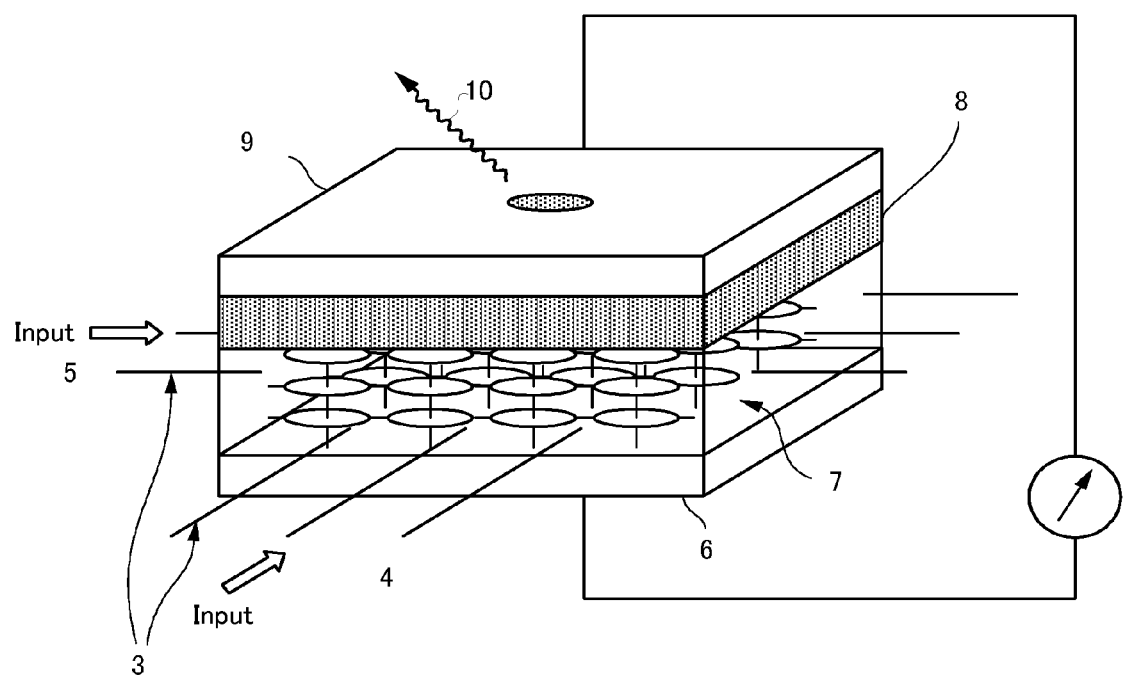
FIG. 3 is a schematic view illustrating an example of a display, in which a multilayered thin film is formed on a substrate, a luminescent molecule layer is laminated on the surface of the thin film, and the luminescent molecule layer is covered with a transparent electrode plate so that a layer, which emits light as electricity is transmitted from the matrix circuit, and luminescence of which is controlled, is formed on the substrate.

Therefore, given that each metal complex of the metal complex chains as a molecular element, and the metal complex chains comprised of the acceptor ligand (conductive wire) are respectively address lines 3 of X direction and Y direction as depicted in FIG. 3, electrode terminals of X-axis 4 and Y-axis 5 are connected to these address lines and each molecular element is made carry the function for transmit an input/output signal. As a result, it is possible to individually switch ON/OFF the molecular elements at the crossing points by the input an electric field of the X-axis 4 and Y-axis 5. Note that, in the laminated structure depicted in FIG. 3, the bottom layer is a substrate electrode 6, the layer above the bottom layer is a matrix layer 7, the layer above the matrix layer is a luminescent molecule layer 8, and the top layer is a transparent electrode 9. Moreover, the arrow directing upwards from the top layer represents emission of light 10, and lines extending along the X-axis 4 and Y-axis 5 represent address lines 3.

By making the metal complex chains have electrically conductive interaction between the metal complex chains in this manner, a fine matrix circuit of a molecular scale is obtained.

<Molecular Functional Device>

Since the metal complex integrated structure has the aforementioned structure and functions, it is applicable to a molecular functional device. As the molecular functional device, those containing the central metal ion of the metal complex in the metal chain and the ligand (conductive wire) and having a multi-layered thin film structure containing two or more kinds of the central metal ion and the ligand (conductive wire) are suitable.

The method for forming the multi-layered thin structure is suitably selected depending on the intended purpose without any restriction. Examples thereof include a method in which a film is formed by repeating the operation of an electrosynthesis or LB method.

As a result of the formation of the multi-layered thin film structure, a molecular functional device of ultra-lattice structure in which two or more molecular layers each having different functions are systematically laminated is obtained. Such molecular functional device is capable of controlling at least one function selected from a change of electronic condition and/or emission of light caused along therewith, memory, structural change, and arithmetic per each molecular.

In the molecular functional device, the metal complex chains thereof may each contain a functional molecular(s) interactive to the metal complex chains at the terminal(s) thereof.

In this case, additional function based on the functional molecule, such as emission of light, memory, structural change, arithmetic and the like, can be imparted to the molecular functional device. Such molecular functional device to which the additional function is imparted is applicable for an arithmetic device, display, memory, and the like.

Figure 4:
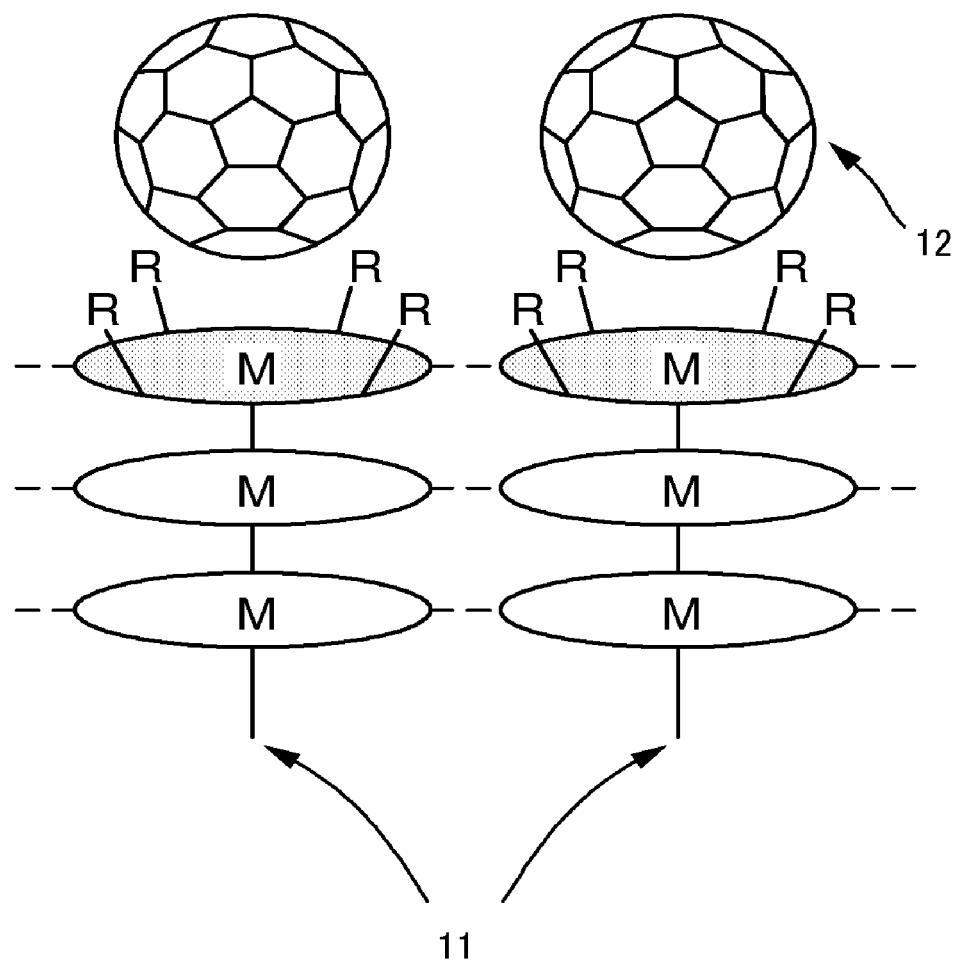
FIG. 4 is a schematic view explaining an example in which, in the matrix circuit (the metal complex integrated structure), a fullerene molecular is captured by the alkyl chain added to the terminal of the metal complex chain.

As a specific example of the molecular functional device to which the functional molecule is introduced at the terminals of the metal complex chains, an embodiment illustrated in FIG. 4 is exemplified. As depicted in FIG. 4, the metal complex chain 11 (the line extending from up to bottom connecting ovals each surrounding "M" in FIG. 4) has an alkyl chain (an alkyl group represented as "R" in FIG. 4) at the terminal thereof, and a fullerene 12 (the structure in the shape of a succor ball in FIG. 4) is captured by the alkyl group.

As another specific example of the molecular functional device to which the functional molecule is introduced at the terminals of the metal complex chains, an embodiment illustrated in FIG. 3 is exemplified. As depicted in FIG. 3, at one terminal of the metal complex chain, a luminescent molecule layer 8, and a transparent electrode 9 are laminated in this order, and a substrate electrode 6 is disposed at the other end of the metal complex chain, to thereby attain a display which is capable of emitting light by the electric conduction from the metal complex chain.

Note that, in this display, no separate conductive connection needs to be individually arranged to each of the metal complex chains, and the display functions just by transmitting electricity between the electrode substrates which sandwich from the top and the bottom. Accordingly, no precise processing and the like are necessary.

Furthermore, an optical characteristic variable layer, molecular structure variable layer or molecule recognition layer may be disposed in place of the luminescent molecule layer, and thus it is possible to design a molecular functional device having a various function.

<Logic Circuit>

Since the metal complex integrated structure has the aforementioned structure and functions, it is applicable to a logic circuit. The metal complex integrated structure has a structure in which the ligand (conductive wire) of the metal complex chain is extended to the edges of the monocrystal and/or thin film. By separating the terminal input parts of the ligands (conductive wires) present in the metal complex integrated structure into several sections, and imparting electric field to each section, a fine logic circuit of molecule scale, which is capable of allowing a certain output in the direction of the metal complex chain can be designed.

FIG. 5 (FIGS. 5A and 5B) are schematic view illustrating examples where the metal complex integrated structure is applied to AND circuit (FIG. 5A) and OR circuit (FIG. 5B) as the logic circuit. Note that, in FIGS. 5A and 5B, the arrows directing from the front to the back represent input A and input B, respectively, the arrows directing upwards represent output C, and an intermediate layer in the three-layered structure is an interchain conductive layer 13.

As illustrated in FIG. 5A, two sections are divided along the direction of one metal complex chain, and the logic circuit is designed so as to be able to input (input A and input B) electric field to each conductive wire in the other metal complex chains, and to output (output C) electric current in the direction of the one metal complex chain. Such logic circuit functions as AND circuit which output (output C) only when there are inputs of both input A and input B, as illustrated in FIG. 5A.

Moreover, as illustrated in FIG. 5B, the conductive layer which transmits electric current to one metal complex chain is inserted, and one of the two sections divided along the direction of the one metal complex chain is further divided along the interchain direction of the one metal complex chain. The logic circuit is designed so as to be able to input (each of input A and input B) the electric field to each of the sections divided in the interchain direction of the one metal complex chain, and to output (output C) the current transmitted on the opposite side of the interchain conductive layer 13 of the one metal complex chain. Such logic circuit functions as OR circuit which output (output C) only when there is input of input A or input B, as illustrated in FIG. 5B.

As described above, various logic circuits can be designed by changing the input method of current. The size of the computing element in the logic circuit is determined depending on the accuracy related to the connection of the electrode terminal. In the case where the terminal is adhered to the crystal with a paste or the like, a large number of molecules are operated as a group. In the case where a signal is applied to each of molecular wires by a scanning tunnel microscopy or the like, it becomes a nano-scale device which operates per molecule.

As has been described above, the metal complex integrated structure formed by crossing the metal complex chains so as to be interacted each other is applicable to a high functional nano-scale device which realizes both a switching element of a molecule-scale and wiring therebetween at the same time. This is based on the self-packing function and/or effect of molecules caused by the self-alignment and/or self-integration of the metal complex chains comprised of the metal complex and the ligand (conductive wire). As result of this, an electronic circuit of the smallest scale which can be physically realized is designed. Moreover, as the metal complex integrated structure has a uniformed lattice structure, the connection accuracy is improved, and a molecular element is suitably operated at any stage, regardless of the size thereof, for example, from the group of a number of molecules to a single molecule, and thus the metal complex integrated structure is applicable to a device of any scale depending on the intended purpose.

The embodiment which is applicable to a cross bar switch (FIG. 6) is described in SCIENCE, vol. 280, pp. 1716-1720, 12 Jun. 1998. Note that, in FIG. 6, α and δ represent an address line and a data line, respectively, and β represents a switch. The address line is used to assign a bit, and once the bit is assigned, the connection between two data lines short-circuits, and the state of the bit is read. The switch may be a semiconductor quantum dot which is connected to two address lines. The semiconductor quantum dot may induce a tunneling or ohmic contact with two data wires. The ligand which connects the semiconductor quantum dot to the four wires controls the property of the connection. This switch is a dual-gate single-electron transistor. Once electric field is imparted to two address lines, the semiconductor quantum dot is sifted to the area outside the Coulomb blockade voltage region, and the date lines are efficiently short-circuited.

According to the embodiments described above, the problems in the art can be solved, and there are provided: a ligand which is capable of constructing a metal complex integrated structure by using only a metal complex unit as a building block without additionally introducing a coupling molecule functioning as a conductive wire portion as well as reducing the molecular weight thereof; a metal complex compound containing the ligand; a method for producing the metal complex compound; and a method for producing a molecular device.

EXAMPLES

Hereinafter, examples of the invention will be described, but these examples shall not be construed to limit the scope of the invention.

Example 1

Synthesis of Ligand 1

As represented in the following synthesis scheme, 10 g of 2-benzoimidazolone was heated and stirred in 100 mL of nitric acid (1.38) at 70° C. for 1 hour, followed by diluting with cold water, to thereby obtain yellow green 5,6-dinitro-2-benzoimidazolone (yield 76.5%). The thus obtained 5,6-dinitro-2-benzoimidazolone was refluxed in phosphorous oxychloride at 140° C. for 7 hours, followed by evaporating the excessive phosphorous oxychloride under reduced pressure, and neutralizing with an aqueous solution of sodium hydrogen carbonate, to thereby obtain yellow 5,6-dinitro-2-chlorobenzimidazole the 2-position of which was chloridized (yield 64.7%).

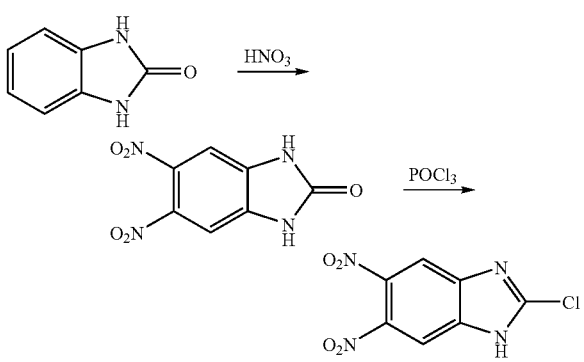

Figure 7:
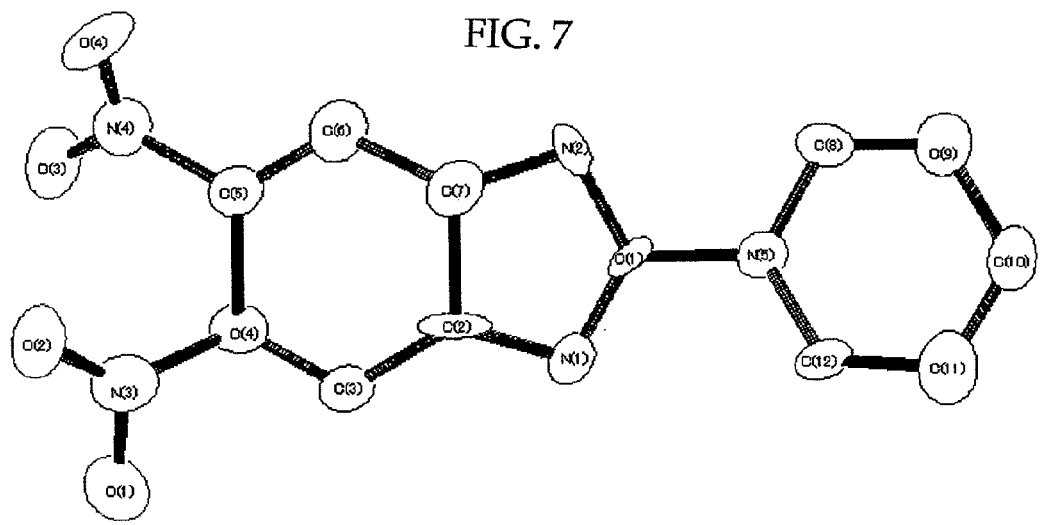
FIG. 7 is a diagram illustrating a structure of a precursor (Formula (1a)) of Ligand 1.

As represented in the following synthesis scheme, the thus obtained 5,6-dinitro-2-chlorobenzimidazole was refluxed in pyridine for 5 hours, followed by condensing, to thereby obtain yellow fine crystals. The thus obtained yellow fine crystals were confirmed to have the structure (Formula (1a)) depicted in FIG. 7 by a monocrystal X-ray structure analysis. The data of the monocrystal X-ray structure analysis is presented below.

<Monocrystal X-Ray Structure Analysis Data>

Crystal system: triclinic system, space group: P1, a=6.216(2), b=8.589(3), c=12.109(5)(Å), α=73.86(3), β=74.69(3), γ=76.71(3)°, V=590.3(5)(Å³)

Figure 8:
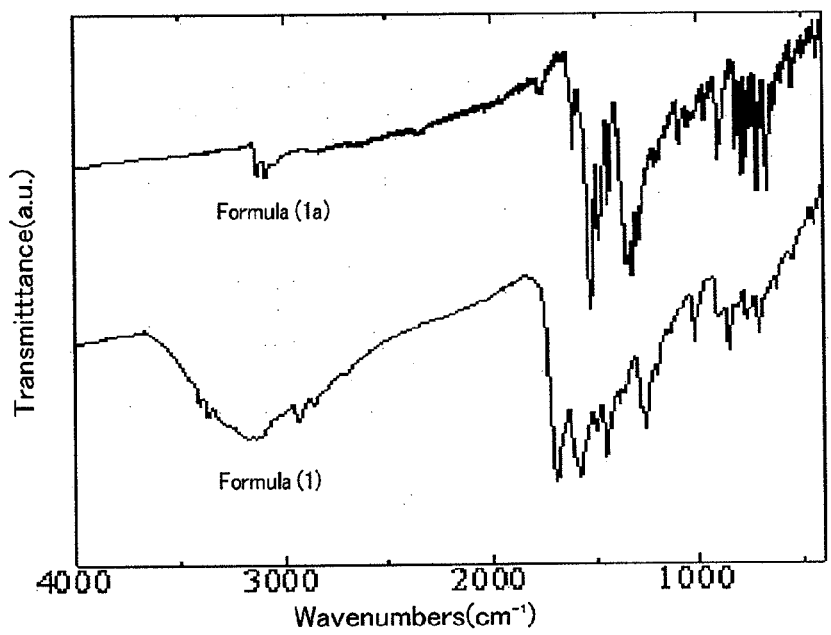
FIG. 8 is a diagram displaying IR spectrum of the precursor (Formula (1a)) of Ligand 1 (Formula (1)).

As represented in the following synthesis scheme, the thus obtained yellow fine crystals were stirred in 2-methoxyethanol solution in the presence of palladium on activated carbon as a catalyst for 5 hours under hydrogen atmosphere, and then the filtrate was condensed by an evaporator to thereby obtain Ligand 1 (Formula (1)) in which nitro groups were replaced with amino groups. Based on IR spectrum, it was confirmed that the nitro groups at the 5- and 6-positions were replaced with amino groups (FIG. 8).

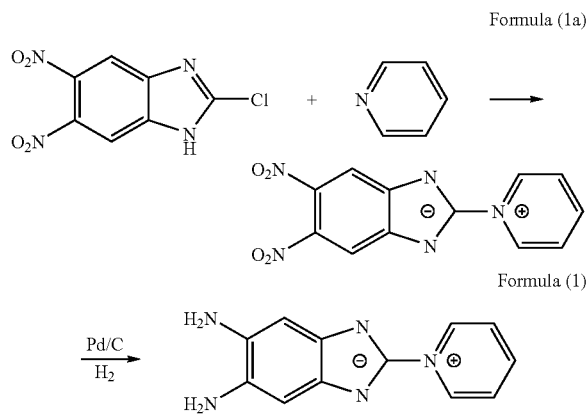

Example 2

Synthesis of Ligand 2

As represented in the following synthesis scheme, 5,6-dinitro-2-chlorobenzimidazole and 4-bromopyridine were stirred in 2-butoxyethanol at 160° C. for 5 hours, followed by condensing, to thereby obtain yellowish brown sediment (Formula (2a)).

Figure 9:
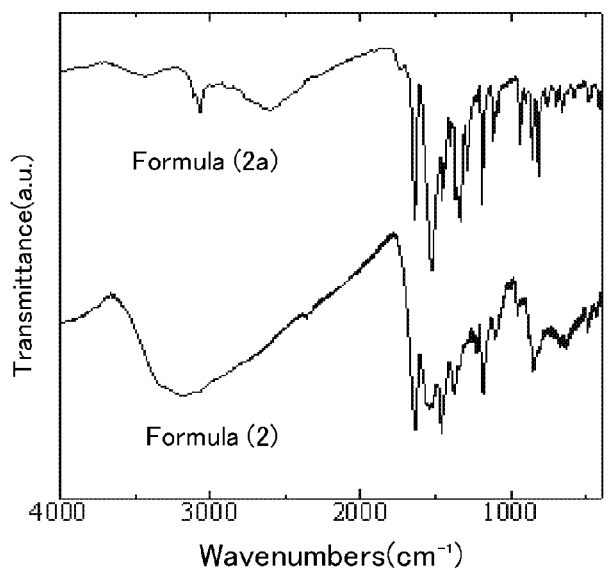
FIG. 9 is a diagram displaying IR spectrum of the precursor (Formula (2a)) of Ligand 2 (Formula (2)).

As represented in the following synthesis scheme, the thus obtained yellowish brown sediment was stirred in 2-methoxyethanol solution in the presence of palladium on activated carbon as a catalyst for 5 hours under hydrogen atmosphere, and then the filtrate was condensed by an evaporator to thereby obtain Ligand 2 (Formula (2)) in which nitro groups were replaced with amino groups. Based on IR spectrum, it was confirmed that the nitro groups at the 5- and 6-positions were replaced with amino groups (FIG. 9).

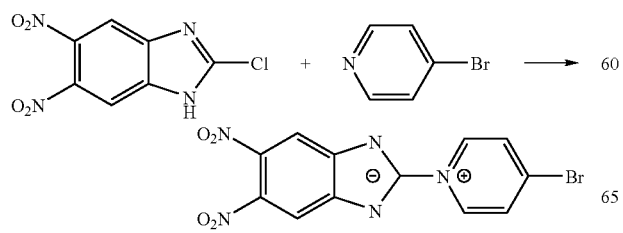

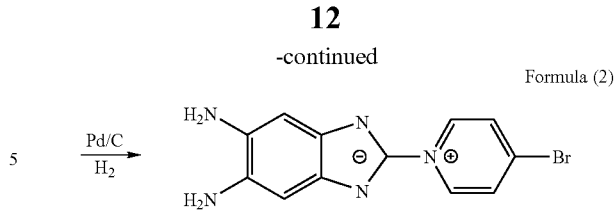

Example 3

Synthesis of Ligand 3

Figure 10:
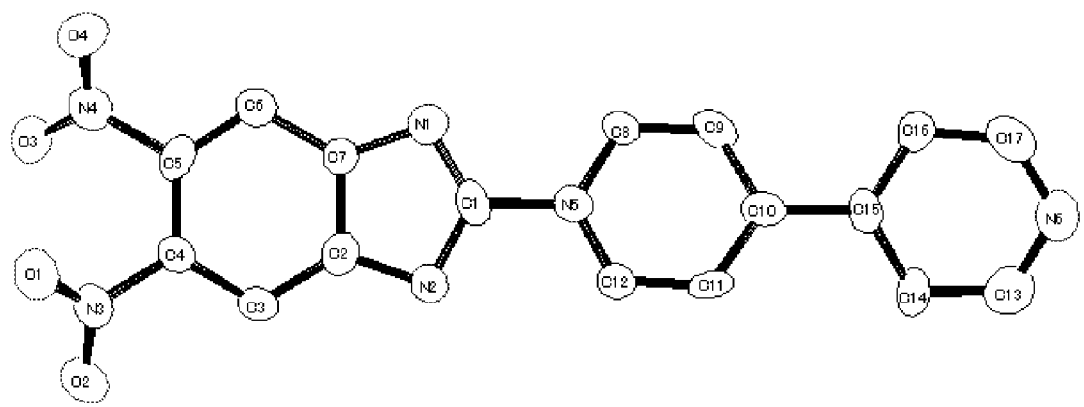
FIG. 10 is a diagram illustrating a structure of a precursor (Formula (3a)) of Ligand 3.

As represented in the following synthesis scheme, 5,6-dinitro-2-chlorobenzimidazole and 4,4'-bipyridinium were stirred in 2-butoxyethanol at 160° C. for 5 hours, followed by condensing, to thereby obtain orange sediment. The thus obtained orange sediment was confirmed to have the structure (Formula (3a)) as depicted in FIG. 10 by monocrystal X-ray structure analysis. The data of the monocrystal X-ray structure analysis is presented below.

<Monocrystal X-Ray Structure Analysis Data>

Crystal system: monoclinic system, space group: P21/a, a=7.791(4), b=22.06(1), c=9.257(5)(Å), α=γ=90, β=107.84(1)°, V=1514.5(1)(Å³).

Figure 11:
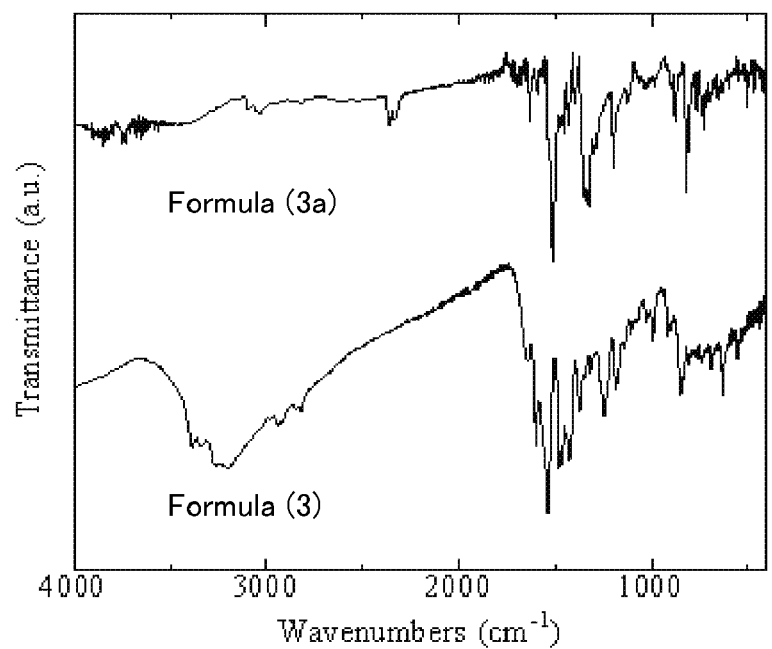
FIG. 11 is a diagram displaying IR spectrum of the precursor (Formula (3a)) of Ligand 3 (Formula (3)).

As represented in the following synthesis scheme, the thus obtained orange sediment was stirred in 2-methoxyethanol solution in the presence of palladium on activated carbon as a catalyst for 5 hours under hydrogen atmosphere, and then the filtrate was condensed by an evaporator to thereby obtain Ligand 3 (Formula (3)) in which nitro groups were replaced with amino groups. Based on IR spectrum, it was confirmed that the nitro groups at the 5- and 6-positions were replaced with amino groups (FIG. 11).

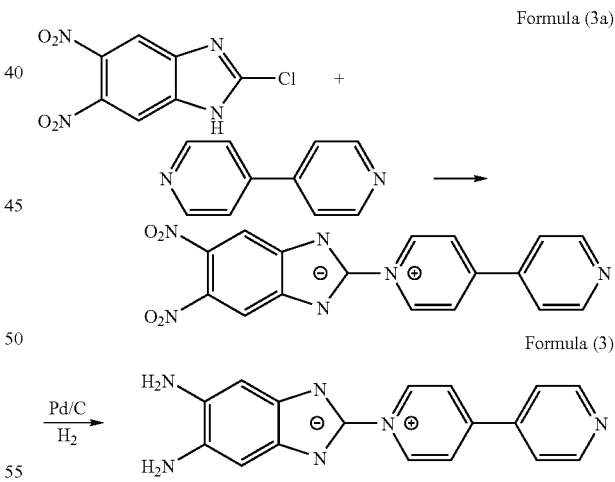

Example 4

Synthesis of Metal Complex 4

Ligand 1 synthesized in Example 1 was stirred together with nickel acetate and palladium on activated carbon in 2-methoxyethanol solution for 5 hours under hydrogen atmosphere, and the filtrate was condensed by an evaporator to thereby obtain a brown nickel complex (Metal Complex 4).

Moreover, by using zinc chloride in place of nickel acetate, a black zinc complex (Metal Complex 4) was obtained.

Example 5

Synthesis of Metal Complex 5

Ligand 2 synthesized in Example 2 was stirred together with nickel acetate and palladium on activated carbon in 2-methoxyethanol solution for 5 hours under hydrogen atmosphere, and the filtrate was condensed by an evaporator to thereby obtain a brown nickel complex (Metal Complex 5).

Moreover, by using zinc chloride in place of nickel acetate, a black zinc complex (Metal Complex 5) was obtained.

Example 6

Synthesis of Metal Complex 6

Ligand 3 synthesized in Example 3 was stirred together with nickel acetate and palladium on activated carbon in 2-methoxyethanol solution for 5 hours under hydrogen atmosphere, and the filtrate was condensed by an evaporator to thereby obtain a brown nickel complex (Metal Complex 6).

Moreover, by using zinc chloride in place of nickel acetate, a black zinc complex (Metal Complex 6) was obtained.

Example 7

Synthesis of Metal Complex 7

Figure 12:
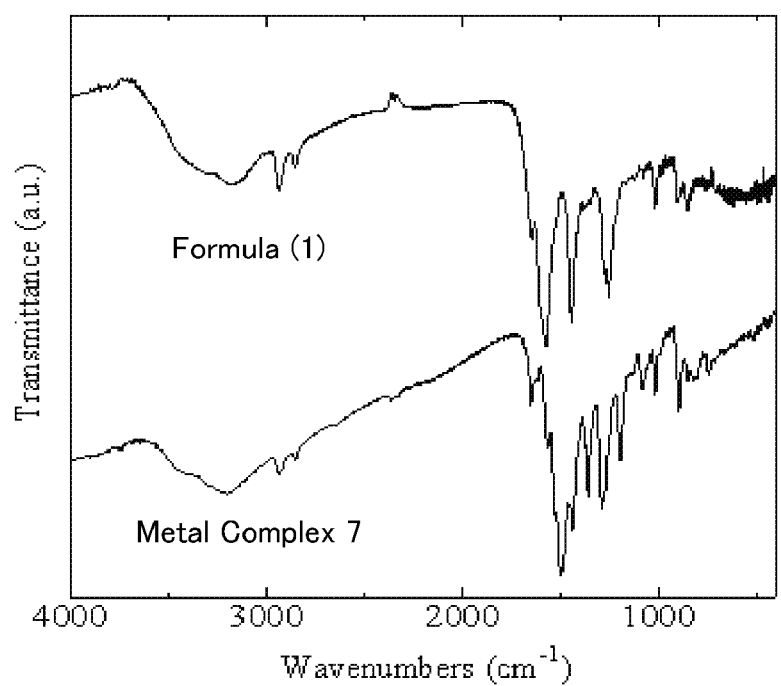
FIG. 12 is a diagram displaying IR spectrum of Ligand 1 (Formula (1)) and Metal Complex 7.

A precursor 1a (Formula (1a)) of Ligand 1 (Formula (1)) was stirred in the presence of palladium on activated carbon as a catalyst in methanol solution for 5 hours under hydrogen atmosphere, to thereby synthesize Ligand 1 (Formula (1)). After filtering this solution, ½ equivalent of nickel acetate/methanol solution was added thereto. As a result, the color of the reaction solution was changed from green to dark blue. By condensing this solution by a rotary evaporator, Metal Complex (nickel complex) 7 of brown sediment was obtained. After measuring IR spectrum (FIG. 12) thereof, it was confirmed that the complex having the structure of Formula (4) in which amino groups of the 5- and 6-positions were coordinated with nickel was formed, as a peak corresponding to a hydrogen bond of the amino group was decreased compared to that of Ligand 1 (Formula (1)).

Example 8

Synthesis of Metal Complex 8

A precursor 2a (Formula (2a)) of Ligand 2 (Formula (2)) was stirred in the presence of palladium on activated carbon as a catalyst in methanol solution for 5 hours under hydrogen atmosphere, to thereby synthesize Ligand 2 (Formula (2)). After filtering this solution, ½ equivalent of nickel acetate/methanol solution was added thereto. As a result, the color of the reaction solution was changed from green to dark blue. By condensing this solution by a rotary evaporator, Metal Complex (nickel complex) 8 of brown sediment was obtained.

Example 9

Synthesis of Metal Complex 9

Figure 13:
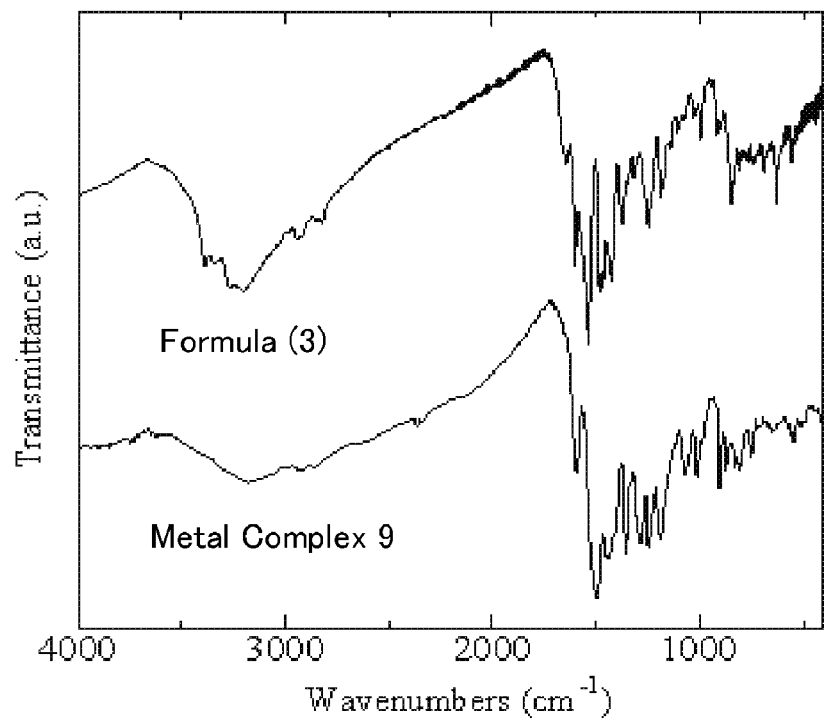
FIG. 13 is a diagram displaying IR spectrums of Ligand 3 (Formula (3)) and Metal Complex 9.

A precursor 3a (Formula (3a)) of Ligand 3 (Formula (3)) was stirred in the presence of palladium on activated carbon as a catalyst in methanol solution for 5 hours under hydrogen atmosphere, to thereby synthesize Ligand 3 (Formula (3)). After filtering this solution, ½ equivalent of nickel acetate/methanol solution was added thereto. As a result, the color of the reaction solution was changed from green to dark blue. By condensing this solution by a rotary evaporator, Metal Complex (nickel complex) 9 of brown sediment was obtained. After measuring IR spectrum (FIG. 13) thereof, it was confirmed that the complex having the structure of Formula (4) in which amino groups of the 5- and 6-positions were coordinated with nickel was formed, as a peak corresponding to a hydrogen bond of the amino group was decreased compared to that of Ligand 3 (Formula (3)).

Example 10

Observation of Redox Chromism

Figure 14:
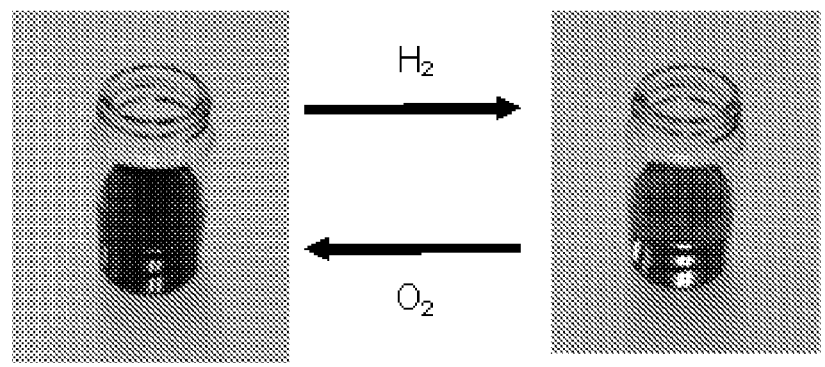
FIG. 14 is a diagram displaying a behavior of redox chromism of Nickel Complex 7.

When airing hydrogen gas in an alcohol solution of nickel complex 7, the color of the solution was changed from dark blue to pale green. After leaving this solution to stand in atmosphere, the color was turned back to dark blue again. As a result, it was found that the solution exhibited redox chromism (chromic phenomenon) (FIG. 14), in which nickel complex 7 was switched by redox.

Figure 15:
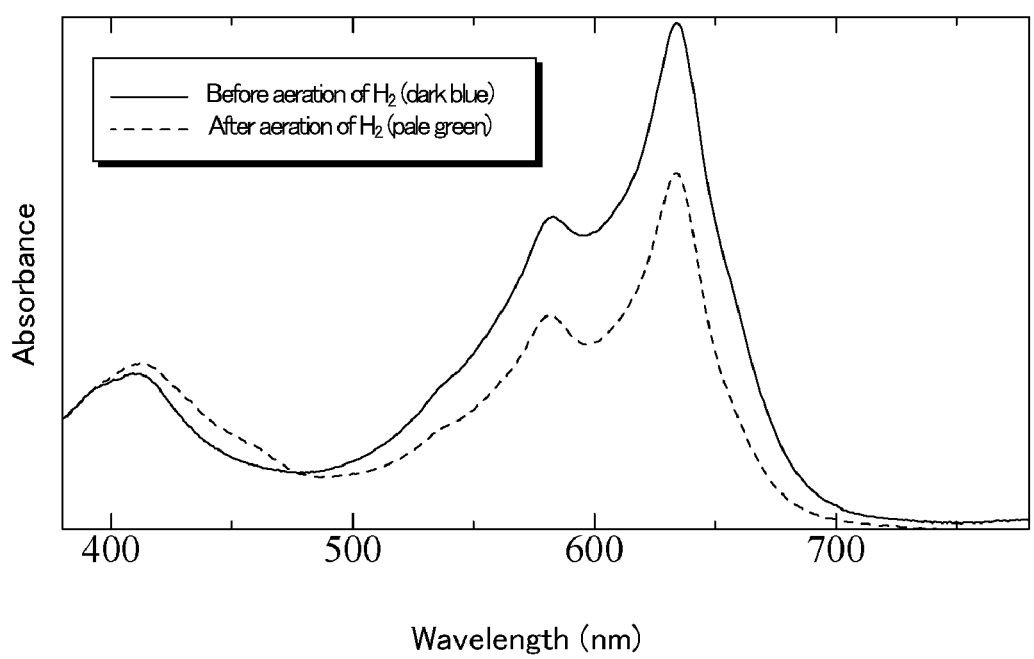
FIG. 15 is a graph displaying a visible absorption spectrum of a methanol solution of Nickel Complex 7.

Furthermore, methanol solution of nickel 7 was subjected to the measurement of visible absorption spectrum (FIG. 15). The dark blue solution before the aeration of hydrogen gas had absorption peaks at 634 nm and 582 nm, but the pale green solution after the aeration of hydrogen gas had the reduced peaks at 634 nm and 582 nm, and thus the redox chromism was confirmed.

The ligand is suitable for a molecular element of ultra-high density and ultra-high operation speed, a matrix circuit, a molecular functional device, a logic circuit, and the like, and is suitably used for a metal complex integrated structure applicable for making various devices in the information communication field, such as computing devices, displays, memories and the like, fine and precise.

All examples and conditional language recited herein are intended for pedagogical purposes to aid the reader in understanding the invention and the concepts contributed by the inventors to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. A ligand expressed by one of the following formulae (1) to (3):

Formula (1)

-continued

Formula (2)

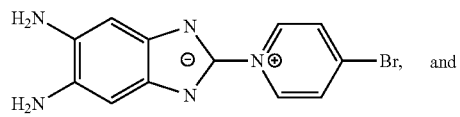

and

Formula (3)

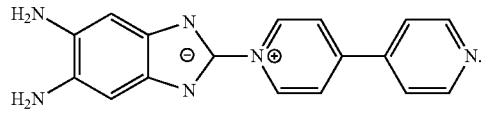

2. A metal complex compound, expressed by the following formula (4):

Formula (4)

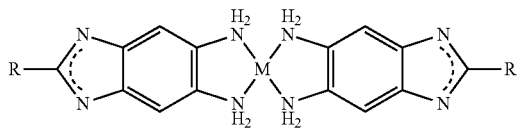

-continued

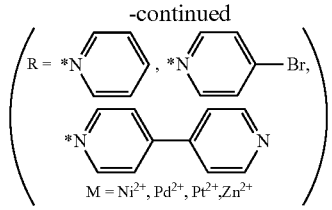

where the asterisk (*) denotes the point of attachment.

3. The metal complex compound according to claim 2, wherein an alcohol solution of the metal complex compound shows redox chromism by aeration of hydrogen gas or air.

4. A method for producing the metal complex compound according to claim 2, comprising:

mixing the ligand of claim 1 and a metal containing solution so as to prepare a mixed solution; and condensing the mixed solution.

* * * * *